US008153151B2

(12) United States Patent
Houze

(10) Patent No.: US 8,153,151 B2
(45) Date of Patent: Apr. 10, 2012

(54) COMPOSITION AND METHOD FOR CONTROLLING DRUG DELIVERY FROM SILICONE ADHESIVE BLENDS

(75) Inventor: David Houze, Coconut Grove, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 575 days.

(21) Appl. No.: 12/286,182

(22) Filed: Sep. 29, 2008

(65) Prior Publication Data

US 2009/0035377 A1 Feb. 5, 2009

Related U.S. Application Data

(63) Continuation of application No. 10/895,688, filed on Jul. 21, 2004, now abandoned.

(60) Provisional application No. 60/488,928, filed on Jul. 21, 2003.

(51) Int. Cl.
*A61F 13/00* (2006.01)
*A61F 13/02* (2006.01)
*A61L 15/16* (2006.01)

(52) U.S. Cl. .................................. 424/449; 424/448
(58) Field of Classification Search .................. 424/449, 424/448
See application file for complete search history.

(56) References Cited

U.S. PATENT DOCUMENTS

| 4,655,767 | A | * | 4/1987 | Woodard et al. ............. 424/448 |
| 6,337,086 | B1 | * | 1/2002 | Kanios et al. ................ 424/449 |
| 2004/0086551 | A1 | * | 5/2004 | Miller et al. ................. 424/449 |

FOREIGN PATENT DOCUMENTS

JP 09169666 A * 6/1997
* cited by examiner

*Primary Examiner* — Isis Ghali
(74) *Attorney, Agent, or Firm* — Foley & Lardner LLP

(57) ABSTRACT

Compositions and methods for controlling transdermal drug delivery, particularly of amine-functional and basic drugs, comprising a blend of a first silicone-based polymer having a reduced silanol concentration and a second silicone-based polymer have a substantial or high silanol concentration. The blend of such silicone-based polymers, particularly pressure-sensitive silicone adhesives, provides sufficient drug solubility and reduced initial drug delivery onset to permit a prolonged delivery duration at a substantially zero-order rate of delivery.

24 Claims, 2 Drawing Sheets

US 8,153,151 B2

COMPOSITION AND METHOD FOR CONTROLLING DRUG DELIVERY FROM SILICONE ADHESIVE BLENDS

CROSS-REFERENCE TO RELATED APPLICATION

This application claims the benefit of U.S. Provisional Application Ser. No. 60/488,928 filed Jul. 21, 2003, which is expressly incorporated by reference in its entirety.

BACKGROUND OF THE INVENTION

1. Field of Invention

The present invention relates to the transdermal delivery of drugs from a silicone-based polymeric mixture. More particularly the present invention relates to methods and compositions for the controlled transdermal delivery of drugs that are otherwise adversely affecting or affected by silicone-based adhesives, such as basic and amine-functional drugs.

2. Description of Related Art

Delivery of certain drugs transdermally has been known to be theoretically possible for many years. However, only limited commercial exploitation of transdermal drug delivery systems has been achieved due in large part to the many practical problems to be overcome with real systems. These problems include the solubility of the drug in the polymeric or adhesive layer, the effect of the drug on the polymeric or adhesive layer, delivery of the drug to the skin and through the stratum corneum at a constant rate over a prolonged period, and stability of the transdermal drug delivery system during storage prior to use.

In seeking to develop transdermal patches that overcome such practical problems, silicone-based adhesives, particularly pressure-sensitive adhesives, have been employed and many are commercially available. Generally, silicone pressure-sensitive adhesives are produced by either blending or condensing a silicone resin and a polydiorganosiloxane. Silicone pressure-sensitive adhesives are known to be non-irritating and non-sensitizing to the skin which is often not true for other polymer-based adhesives such as acrylics.

Currently, amine compatible silicone pressure-sensitive adhesives are used commercially for transdermal delivery of fentanyl. These systems require the use of ethanol containing reservoirs and rate controlling membranes to achieve controlled drug permeation.

However, fentanyl and other amine-functional drugs including, for example nitroglycerin, scopolamine, clonidine, nicotine, tetracain, ramipril and enalapril, that are desirable to be delivered transdermally can interact with silicone adhesives by acting as catalysts for the condensation of silicone-bonded hydroxyl groups (thereby resulting in loss of cohesivity and adhesivity) or be degraded/destabilized in the presence of such hydroxy groups.

U.S. Pat. No. RE 35,474 teaches that amine-functional drugs interfere with the properties of pressure-sensitive adhesives by catalyzing the reaction of silicone-bonded hydroxyl (silanol) groups and, thereby, cause increased increase shear of the pressure-sensitive adhesive material and, thus, loss of tack during storage. This reference teaches that this effect can be inhibited by chemically treating the pressure-sensitive adhesives with an agent to reduce their silanol content.

U.S. Pat. No. 6,337,086 teaches that the amount of agent used to treat the silicone pressure-sensitive adhesive material as disclosed in U.S. Pat. No. RE 35,474 may result in a silanol content that is too low, and therefore an adhesive that is plasticized and oozy. Accordingly, to achieve the adhesive performance properties (i.e., peel and shear) necessary for transdermal applications, such silicone pressure-sensitive adhesive materials must be prepared with well-defined silanol concentrations.

However, in formulating a simplified drug-in-adhesive transdermal system (i.e., wherein the adhesive functions as both the drug carrier and means of attachment to the topical application site), incorporating fentanyl directly into an amine compatible silicone pressure-sensitive adhesive results in crystallization of the drug and therefore loss of bioavailability.

Therefore, it would be advantageous to find a silicone-based adhesive system that can solubilize sufficient amounts of drugs that are otherwise adversely affecting or affected by such silicone-based adhesives, and that can permit drug release in a controlled fashion over a prolonged period at a steady rate of delivery.

SUMMARY OF THE INVENTION

It is the object of the present invention to provide compositions and methods for delivering active agents and, in particular, amine-functional and basic drugs, that are otherwise adversely affecting or affected by silicone-based polymers in adhesive compositions of transdermal systems, that reliably prevent/inhibit crystallization of the active agent and achieve controlled and constant release rates over a pre-determined application duration, particularly for 3 days or more. These and other objects of the invention are achieved by blending a silicone-based polymer having a substantial silanol concentration with a silicone-based polymer having a reduced silanol concentration.

DETAILED DESCRIPTION OF THE PREFERRED EMBODIMENTS

Figure 1:
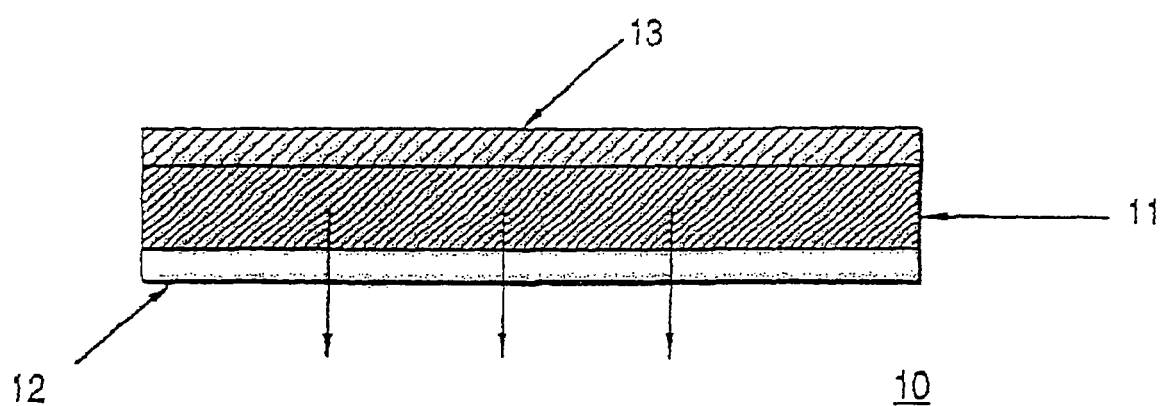
FIG. 1 is a schematic illustration of a monolithic or adhesive matrix transdermal drug delivery system of the present invention
Figure 2:
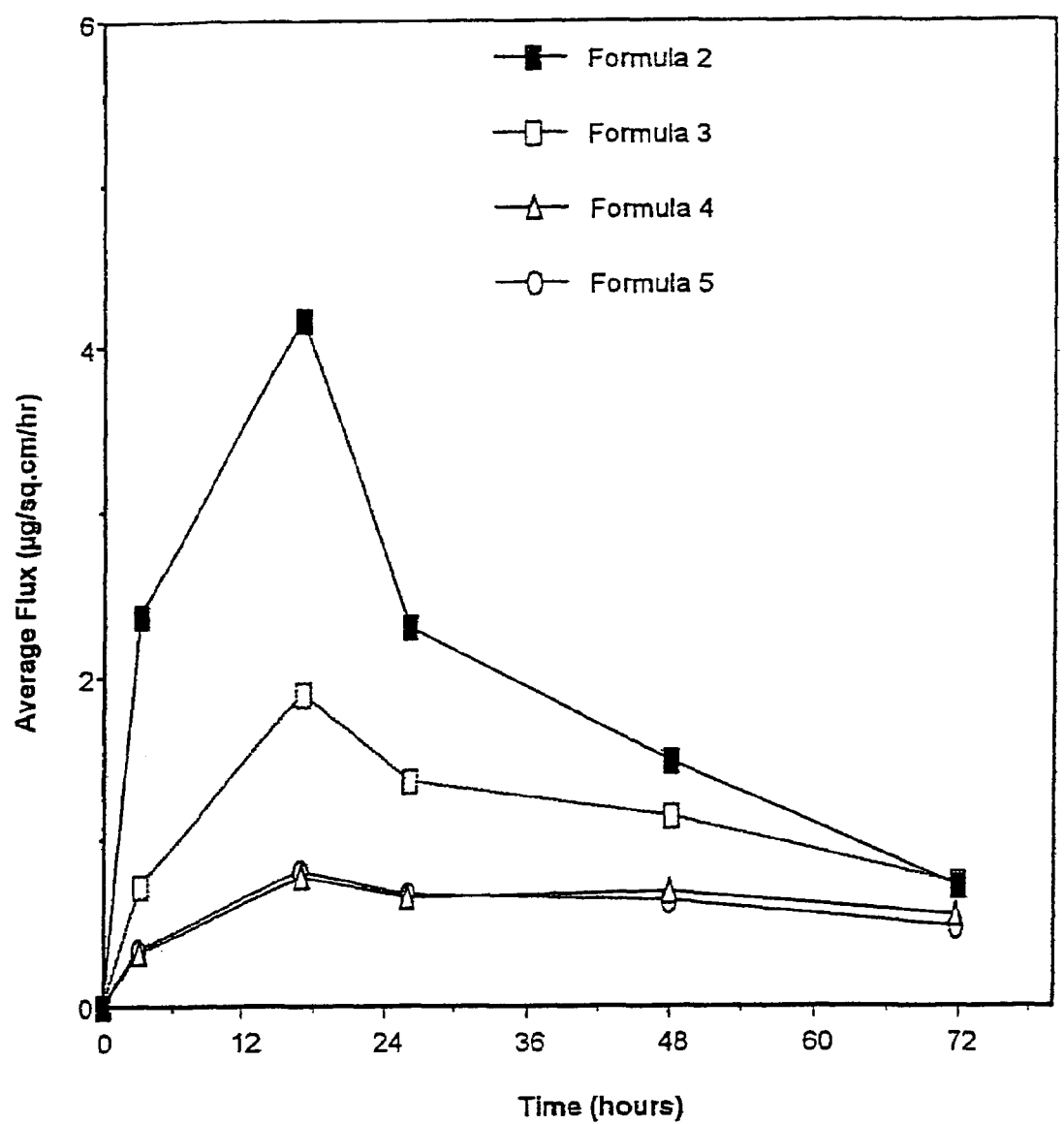
FIG. 2 is a graphical representation of average fentanyl flux through cadaver skin from an in-vitro permeation study over 72 hours of transdermal adhesive systems comprising various weight ratios of silicone-based adhesives, illustrating the type of delivery kinetics which can result from experimental modifications of the silicone-based polymers in the formulations presented in Table I.

The present invention is based on the unexpected discovery that the delivery rate of certain drugs can be controlled by means of incorporating such drug in a mixture of at least two silicone-based polymers. Specifically, the desired delivery rate of amine-functional and basic drugs can be achieved by blending a silicone-based polymer having a substantial silanol concentration with a silicone-based polymer having a reduced silanol concentration. It has been discovered that the addition of the silicone-based polymer having a substantial silanol concentration to a silicone-based polymer having a reduced silanol concentration provides sufficient solubility for the drug and retards or reduces the delivery rate of the drug, thereby permitting a prolonged duration of drug administration at a substantially zero-order rate of delivery with such a mixture, while maintaining acceptable adhesive and cohesive properties.

The phrase "substantially zero-order" as used herein means transdermal delivery of a drug through the skin or mucosa at a rate that is approximately constant once steady state is attained. Typical variability contemplated within the scope of this meaning is about a 30% to about 40% difference from the mean in the blood levels of drug at steady state, typically reached within 24 or less hours after topical application.

As used herein, the term "transdermal" is intended to mean delivery of a drug by passage into and through the skin or mucosal tissue and is used interchangeably with the terms transmucosal and percutaneous unless specifically stated otherwise.

The term "amine-functional" is intended to mean a drug or active agent that can contain one or more primary amine radicals such as phenylpropanolamine, secondary amine radicals such as propranolol, tertiary amine radicals such as theophylline and chlorpheniramine. The term "amine-functional" also includes heterocyclic amine radicals such as those found in theophylline and diethylcarbomazine and salts of amine-functional drugs such as scopolamine hydrobromide provided that they can be delivered transdermally, but does not include oxidized nitrogen radicals such as nitro radicals. Other examples of amine-functional drugs for transdermal drug delivery include, for example, tetracain, ephedrine, clonidine, nicotine, ramipril, enalapril, fentanyl and analogs such as alfentanyl, carfentanyl, lofentanyl, remifentanyl, sufentanyl, and trefentanyl, amphetamine, dextroamphetamine, methamphetamine, and atropine. Further examples of amine-functional drugs for use in transdermal drug delivery systems will be apparent to those skilled in the art.

The term "basic drug" is intended to mean a drug or active agent that is a free base or a pharmaceutically acceptable prodrug and salts thereof. Preferred basic drugs are strongly basic drugs with a $pK_a$ of about 8 or greater. Preferred examples of basic drugs that can be delivered by the transdermal system of the present invention include oxybutynin, scopolamine, fentanyl and its analogs, fluoxetine, epinephrine, morphine, hydromorphone, atropine, cocaine, buprenorphine, chlorpromazine, imipramine, desipramine, methylphenidate, methamphetamine, lidocaine, procaine, benzocaine, tetracaine, pindolol, nadolol, carisoprodol, azelastine, tacrine, alprazolam, buspirone, paroxetine, pramipaxole, bupropion, clonazepam, timolol, cyclobenzaprine, granisetron, levorphanol, triptans, pergolide, ropinirole, rotigotine, and acid addition salts thereof. Fentanyl and sufentanyl base and acid addition salts thereof are more preferred while selegiline base is not preferred. Drug concentration for use according to the present invention is drug dependent, but typically is below about 20% by dry weight of the composition, and more preferably below 10%.

The silicone-based polymers having a reduced or low silanol concentration for use in the method and device of the present invention are generally those with a silicone-bonded hydroxyl content of about 13,000 or less, and preferably below about 7,700. Preferred silicone-based polymers having a reduced silanol are amine compatible. As used herein, the term "amine compatible" is intended to mean a silicone polymer wherein the silicone-bonded hydroxyl groups (Si—OH) have been substantially reduced or eliminated, typically by substitution with a hydrocarbon radical such as a methyl group (Si—CH$_3$).

The silicone-based polymers having a substantial or high silanol concentration for use in the method and device of the present invention are generally those that have not been chemically treated to reduce or eliminate their silanol groups and/or have a silicone-bonded hydroxyl content of greater than about 13,000.

Preferred silicone-based polymers are adhesives (capable of sticking to the site of topical application), particularly pressure-sensitive adhesives. A polymer is an adhesive within the meaning of the term is it has the properties of an adhesive per se or if it functions as an adhesive by the addition of tackifiers, plasticizers, crosslinking agents or other additives. Illustrative examples of silicone-based polymers having reduced silanol concentrations are amine compatible silicone-based adhesives (and capped polysiloxane adhesives) such as those described in U.S. Pat. No. Re. 35,474 and U.S. Pat. No. 6,337,086, incorporated herein by reference, and which are commercially available from Dow Corning Corporation under their BIO-PSA 7-4100, -4200 and -4300 product series. Illustrative examples of silicone-based polymers having a substantial silanol concentration include such silicone-based adhesives that are commercially available from Dow Corning Corporation under their BIO-PSA 7-4400, -4500, and -4600 product series.

The transdermal devices contemplated for practicing the methods and devices of the present invention are in the form of a flexible, finite system, and many such devices are known in the art as well as being commercially available. The phrase "flexible, finite system" is intended to mean a substantially non-aqueous, solid form capable of conforming to the surface with which it comes into contact, and which is capable of maintaining the contact in such solid form so as to facilitate topical application without adverse physiological response, and without being appreciably decomposed by aqueous contact during topical application to a patient.

Suitable flexible, finite delivery systems include those in which the drug is solubilized or contained directly in an adhesive matrix, typically a preferably a pressure-sensitive adhesive, that also serves as the means for attachment to the skin or mucosa of a patient. In addition to this adhesive drug layer, a drug-in-adhesive or matrix transdermal system further comprises a drug impermeable backing layer or film on one side of the adhesive layer, and a release liner on the other side. The backing layer protects the adhesive layer of the transdermal patch from the environment and prevents loss of the drug and/or release of other adhesive layer components to the environment. The release liner is removed from the transdermal patch to expose the adhesive layer prior to topical application.

Reference to FIG. 1 shows a schematic illustration of a drug-in-adhesive or adhesive matrix device embodiment of the invention 10. The transdermal system comprises a monolithic body 11 of a defined geometric shape with a protective release liner 12 on one side of monolithic body 11 and a backing layer 13 on the other side. Removal of the release liner 12 exposes the pressure-sensitive multiple polymer adhesive which functions both as the drug carrier matrix and as the means of applying the system to the patient.

Illustrative examples of making such transdermal systems are described in U.S. Pat. Nos. 5,474,783, and 5,656,286 both assigned to Noven Pharmaceuticals, Inc., Miami, Fla. (incorporated herein by reference), and drug-in-adhesive or matrix transdermal systems according to the present invention should be considered to comprise such backing layer and release liner or their functional equivalents.

A particularly preferred embodiment comprises an adhesive/matrix layer comprising a blend of an amine-compatible silicone-based pressure-sensitive adhesive with a silicone-based pressure-sensitive adhesive having a substantial silanol concentration, wherein such adhesive is in an amount of about 10% to about 80%, more preferably from about 20% to about 75%, and even more preferably from about 25% to about 60%, based on the dry weight % of the total adhesive/matrix layer, and wherein the drug is fentanyl base.

Other flexible, finite systems known in the art include films, plasters, dressings, and bandages, multilayer delivery systems in which the drug is solubilized or contained in one or more separate layers, and reservoir-type delivery systems in which the drug is solubilized or contained in a reservoir or depot separate form the adhesive which attaches directly to the skin or mucosa including those with an outer or in-line/overlay adhesive.

The transdermal system can further comprise various pharmaceutically acceptable ingredients in addition to the silicone-based polymer blend and basic drug provided that such additive ingredients do not materially alter the basic and novel characteristics of the transdermal patch. Such additives are generally known in the art of drug delivery and, more particularly, in the art of transdermal drug delivery, and include, for example, agents known to accelerate the delivery of a drug through the skin. These agents have been referred to as skin-penetration enhancers, accelerants, adjuvants, and sorption promoters, and are herein referred to collectively as "enhancers." This class of agents includes those with diverse mechanisms of action including those which have the function of improving the solubility and diffusibility of a drug within the multiple polymer and those which improve percutaneous adsorption, for example, by changing the ability of the stratum corneum to retain moisture, softening the skin, improving the skin's permeability, acting as penetration assistants or hair-follicle openers or changing the state of the skin including the boundary layer. Some of these agents have more than one mechanism of action, but in essence they serve to enhance the delivery of a drug.

Some examples of enhancers are polyhydric alcohols such as dipropylene glycol, propylene glycol, and polyethylene glycol which enhance drug solubility; oils such as olive oil, squalene, and lanolin; fatty ethers such as cetyl ether and oleyl ether; fatty acid esters such as isopropyl myristate which enhance drug diffusibility; urea and urea derivatives such as allantoin which affect the ability of keratin to retain moisture; polar solvents such as dimethyldecylphosphoxide, methyloctylaulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate. In the preferred embodiment of the present invention, enhancers are however not necessary or even desired.

In addition, the solubility of the drug can be further altered by the optional addition of an agent which increases the solubility of drug or inhibits drug crystallization in the transdermal composition, such as polyvinylpyrrolidone, vinyl acetate/vinylpyrrolidone copolymer and cellulose derivatives, and are herein referred to collectively as "crystallization inhibitors." Use of such agents are preferred for controlling delivery of amine-functional drugs instead of increasing the amount of the silicone-based polymer having substantial or high silanol concentration. In such drug delivery compositions, the amount of such silicone-based polymer having substantial or high silanol concentration, particularly amine compatible silicone-based polymers, should be kept below about 50% by dry weight of the total composition to avoid potential drug crystallization.

EXAMPLES

The following specific examples are included as illustrative of topical systems and compositions within the contemplation of the invention. These examples are in no way intended to be limiting of the scope of the invention. Other aspects of the invention will be apparent to those skilled in the art to which the invention pertains. The weight percentages in the examples are based on dry weight of the total transdermal composition, unless otherwise noted.

As used herein, the term, "flux" is defined as the absorption of the drug through the skin or mucosa, and is described by Fick's first law of diffusion:

$$J = -D(dCm/dx),$$

where J is the flux in $g/cm^2/sec$, D is the diffusion coefficient of the drug through the skin or mucosa in $cm^2/sec$ and Dcm/dx is the concentration gradient of the drug across the skin or mucosa.

The following commercially available products were used in the example: "BIO-PSA 7-4202 and 7-4502 are trademarks of Dow Corning Corporation, Medical Products, Midland, Mich., for polysiloxane pressure-sensitive adhesives in organic solutions.

The fentanyl base was obtained from Mallinckrodt, Inc., St. Louis, Mo.

The silicone-based adhesive blends with drug formulations shown in Table I were prepared as follows. A mixture of 0.008 g of fentanyl base was combined in a container with varying amounts of an amine compatible silicone adhesive (BIO-PSA 7-4202 at 4.86 g, 3.65 g, 2.43 g, 1.22 g, and 0.0 g) and/or a silicone adhesive having a substantial silanol concentration (BIO-PSA 7-4502 at 0.0 g, 1.21 g, 2.41 g, 3.61 g, and 4.83 g, respectively), and with 0.24 g of toluene, and rotated overnight until thoroughly mixed.

TABLE I

| COMPONENT | FORMULA NUMBER | | | | |
| --- | --- | --- | --- | --- | --- |
| | 1 | 2 | 3 | 4 | 5 |
| Fentanyl | 2.5 | 2.5 | 2.5 | 2.5 | 2.5 |
| BIO-PSA ® 7-4202 (reduced silanol conc.) | 97.5 | 72.5 | 47.5 | 22.5 | 0 |
| BIO-PSA ® 7-4502 (substantial silanol conc.) | 0 | 25.0 | 50.0 | 75.0 | 97.5 |

Each polymeric blend was then cast onto a silicon coated release liner (Scotchpak™ 1022 release liner manufactured by 3M™) and drawn down using a Gardner fixed gap applicator to about a 15 ml thickness. The coated release liner was dried for 5 minutes at room temperature, then for 5 minutes at 92° C. in a convection oven in order to drive off the volatile solvents. The dried matrix was pressure laminated to the polyester side of a polyester/ethylene vinyl acetate backing film (Scotchpak™ 9732 backing material manufactured by 3M™) with a resulting coat weight of 10.0+/−0.5 $mg/cm^2$.

Flux studies using human cadaver skin were conducted with stratum corneum obtained from split thickness cryopreserved cadaver skin by the heat separation technique (Kligman & Christopher, 88 Arch. Dermatol. 702 (1963), hereby incorporated by reference, involving treating the full thickness cadaver skin at 60° C. for 60 seconds, after which time the stratum was gently peeled from the dermis).

Three samples of each laminated formulation were next cut into 0.5 cm² circular pieces, the release liner removed and placed upon stratum corneum. The skin-matrix samples were then mounted between the donor and receiver compartments on modified Franz cells, the skin side facing the receiver compartment containing a receiving solution of 7.5 ml of 0.9% NaCl and 0.01% $NaN_3$ magnetically stirred at about 300 rpm. The Franz cells were then placed in an incubator to maintain the samples at 32° C. At predetermined sampling intervals, the entire contents of the receiver compartment were collected for drug assaying, and the receiver compartments refilled with fresh receiving solutions.

The permeation samples were then analyzed by HPLC using a Phenomenex® Columbus C8, 5 µm, 10.0×0.46 cm column with a flow rate of 1.5 ml/min. with the detector is set at 210 nm.

The column mobile phase was: buffer:acetonitrile:methanol (50:30:20). The buffer is 10 mM $KH_2PO_4$+4.5 mM OSA at pH 3.0.

Drug crystallized in formula 1 and therefore this formulation could not be included in the flux study. The results of the skin flux experiments over the duration of the three day study for the remaining four formulas are presented in Table II. FIG. 1 illustrates the results obtained for drug permeation from the 4 remaining formulas.

TABLE II

| FORMULA NUMBER | PERMEATION RATE (µG/CM²) |
|---|---|
| 2 | 1.92 |
| 3 | 1.20 |
| 4 | 0.65 |
| 5 | 0.62 |

These results show that fentanyl permeation is slowed as the silanol content of the silicone adhesive matrix increases, and strongly suggests that that the solubility parameters of such silicone adhesives differ substantially enough to permit effective manipulations of drug release rates through human cadaver skin, similar to results found when blending silicone and acrylic pressure-sensitive adhesives. While use of silicone-based adhesives having a reduced silanol concentration may provide a fast onset with first order delivery, many drug therapies require a substantially zero-order delivery for an extended duration which cannot be achieved with such silicone adhesives alone as evidenced by the results. Moreover, the permeation rate under in-vivo conditions would be too high to be able to prevent side effects caused by excessive plasma levels, particularly critical in the case of fentanyl. FIG. 1 demonstrates prolonged duration at a substantially zero-order delivery from the transdermal system of the present invention. Consequently, simple silicone blends have the ability to control and manipulate drug release rates effectively with very low irritation potential.

What is claimed is:

1. A method of selectively controlling transdermal drug delivery, comprising topically administering at least one drug in a flexible, finite matrix, said matrix comprising a blend of:
    (i) at least one first silicone-based polymer, said first silicone-based polymer having a silicone-bonded hydroxyl content below about 13,000;
    (ii) at least one second silicone-based polymer, said second silicone-based polymer having silicone-bonded hydroxyl content of greater than about 13,000, and
    (iii) at least one drug present in an amount sufficient to achieve kinetics resulting in blood levels of drug that is approximately constant once steady state is attained, wherein the relative amounts of said at least one first silicone-based polymer and said at least one second silicone-based polymer are selected to control the onset and rate of delivery.

2. The method according to claim 1, wherein said first silicone-based polymer has a silicone-bonded hydroxyl content below about 7,700.

3. The method according to claim 1, wherein said at least one drug includes a basic drug.

4. The method according to claim 1, wherein the matrix further comprises at least one additive selected from the group consisting of enhancers and crystallization inhibitors.

5. The method according to claim 4, wherein said crystallization inhibitor is selected from the group consisting of polyvinylpyrrolidone, vinyl acetate/vinylpyrrolidone copolymer and cellulose derivatives.

6. The method according to claim 1, wherein said second silicone-based polymer is present in an amount below about 50% by dry weight of said matrix.

7. The method according to claim 1, wherein the relative amounts of said at least one first silicone-based polymer and said at least one second silicone-based polymer are selected such that the blood levels of said patient do not vary more than about 40% from the mean at steady state for delivery to the skin or mucosa of a patient in need thereof over a period of at least 72 hours.

8. The method according to claim 1, wherein said at least one drug is selected from the group consisting of oxybutynin, scopolamine, clonidine, nicotine, ramipril, enalapril, fentanyl and fentanyl analogs fluoxetine, epinephrine, morphine, hydromorphone, atropine, cocaine, buprenorphine, chlorpromazine, imipramine, desipramine, methylphenidate, amphetamine, dextroamphetamine, phentermine, methamphetamine, lidocaine, procaine, benzocaine, tetracaine, pindolol, nadolol, carisoprodol, azelastine, tacrine, alprazolam, buspirone, paroxetine, pramipaxole, bupropion, clonazepam, timolol, cyclobenzaprine, granisetron, levorphanol, non-steroidal anti-inflammatory agents triptans, pergolide, ropinirole, rotigotine, testosterone, and acid addition salts thereof.

9. The method according to claim 8, wherein said at least one drug includes fentanyl and/or one or more analogs thereof.

10. The method according to claim 1, wherein said at least one drug includes an amine-functional drug.

11. The method according to claim 1, wherein said at least one second silicone-based polymer is present in an amount from about 10% to about 80% by dry weight of said matrix.

12. The method according to claim 1, wherein said at least one said second silicone-based polymer is present in an amount from about 20% to about 75% by dry weight of said matrix.

13. The method according to, claim 1, wherein said at least one said second silicone-based polymer is present in an amount from about 25% to about 60% by dry weight of said matrix.

14. The method according to claim 9, wherein said fentanyl and analogs thereof are in free base form.

15. The method according to claim 1, wherein:
    said at least one drug comprises at least one amine-functional drug;
    said at least one first silicone-based polymer is present in an amount of from about 22.5% to about 72.5% by dry weight of said matrix; and said at least one second silicone-based polymer is present in an amount of from about 25% to about 75% by dry weight of said matrix.

16. The method according to claim 15, wherein said at least one amine-functional drug is selected from the group consisting of oxybutynin, scopolamine, ephedrine, clonidine, nicotine, ramipril, enalapril, fentanyl and fentanyl analogs fluoxetine, epinephrine, morphine, hydromorphone, atropine, cocaine, buprenorphine, chlorpromazine, imipramine, desipramine, methylphenidate, amphetamine, dextroamphetamine, methamphetamine, lidocaine, procaine, tetracaine, pindolol, nadolol, carisoprodol, and acid addition salts thereof.

17. The method according to claim 16, wherein said at least one amine-functional drug includes fentanyl and/or one or more analogs thereof.

18. The method according to claim 17, wherein said fentanyl and analogs thereof are in free base form.

19. The method according to claim 15, wherein the matrix further comprises at least one additive selected from the group consisting of enhancers and crystallization inhibitors.

20. The method according to claim 19, wherein said crystallization inhibitor agent is selected from the group consisting of polyvinylpyrrolidone, vinyl acetate/vinylpyrrolidone copolymer, and cellulose derivatives.

21. The method according to claim 20, wherein said at least one second silicone-based polymer is present in an amount below about 50% said matrix.

22. A flexible, finite transdermal drug delivery composition, said composition comprising a blend of:
a matrix and at least one drug,
wherein said matrix consists essentially of:
a first silicone-based polymer in an amount of from about 22.5% to about 72.5% by dry weight of said matrix, said first silicone-based polymer having a silicone-bonded hydroxyl content of below about 13,000;
a second silicone-based polymer in an amount below about 50% by dry weight of said matrix, said second silicone-based polymer having a silicone-bonded hydroxyl content of greater than about 13,000; and a crystallization inhibition agent selected from the group consisting of polyvinylpyrrolidone, vinyl acetate/vinylpyrrolidone and cellulose derivatives;
wherein said at least one drug is selected from the group consisting of fentanyl, alfentanyl, carfentanyl, lofentanyl, remifentanyl, sufentanyl, trefentanyl, amphetamine, paroxetine pramipexole, rotigotine and azelastine, and is present in an amount sufficient to achieve kinetics resulting in blood levels of drug that do not vary more than about 40% from the mean at steady state for delivery to skin or mucosa of a patient in need thereof over a period of time of at least 72 hours.

23. The method according to claim 8, wherein said fentanyl analog is selected from the group consisting of alfentanyl, carfentanyl, lofentanyl, remifentanyl, sufentanyl, and trefentanyl.

24. The method according to claim 8, wherein said non-steroidal anti-inflammatory agent is ketoprofen.

* * * * *